(12) United States Patent
Stewart et al.

(10) Patent No.: US 7,795,491 B2
(45) Date of Patent: Sep. 14, 2010

(54) SYSTEMS AND METHODS FOR COUNTING SURGICAL IMPLEMENTS

(75) Inventors: Brian E. Stewart, Santa Monica, CA (US); Nicolas Soichet, Marina Del Rey, CA (US)

(73) Assignee: Patient Safety Technologies, Inc., Los Angeles, CA (US)

(*) Notice: Subject to any disclaimer, the term of this patent is extended or adjusted under 35 U.S.C. 154(b) by 306 days.

(21) Appl. No.: 11/347,490

(22) Filed: Feb. 3, 2006

(65) Prior Publication Data

US 2007/0083170 A1 Apr. 12, 2007

Related U.S. Application Data

(60) Provisional application No. 60/725,960, filed on Oct. 11, 2005.

(51) Int. Cl.
*A61F 13/15* (2006.01)
*A61F 13/20* (2006.01)

(52) U.S. Cl. .................. 604/358; 235/375; 235/376; 235/377; 235/385; 235/424; 235/425; 235/431; 235/437; 235/462.01; 235/462.04; 235/462.12; 235/462.13; 235/462.45; 235/462.49; 235/469; 235/472.01; 235/472.03; 235/494; 340/539.12; 340/539.32; 340/571; 340/572.1; 340/592; 340/10.42; 340/286.07; 700/1; 700/27; 700/236; 700/109; 700/115; 700/224; 700/225; 700/226; 700/227; 705/2; 705/3; 705/7; 705/308; 705/317; 705/333; 707/653; 707/609

(58) Field of Classification Search .................. 604/358; 235/375, 376, 377, 385, 424, 425, 431, 437, 235/462.01, 462.04, 462.12–462.13, 462.45, 235/462.49, 469, 472.01, 472.03, 494; 340/539.12, 340/539.32, 571, 572.1, 592, 10.42, 286.07; 700/1, 27, 236, 109, 115, 224–227; 705/2, 705/3, 7, 308, 317, 333; 707/653, 609
See application file for complete search history.

(56) References Cited

U.S. PATENT DOCUMENTS 3,941,132 A 3/1976 Lenaghan (Continued)

FOREIGN PATENT DOCUMENTS

EP 0948940 10/1999

(Continued)

OTHER PUBLICATIONS

Association of Operating Room Nurses, AORN Journal; Feb. 2006; 83, 2; pp. 418-433. Origninally published May 1976, AORN Journal, as "Standards for Sponge, Needle, and Instrument Procedures."*

(Continued)

*Primary Examiner*—Tatyana Zalukaeva
*Assistant Examiner*—Ginger T Chapman
(74) *Attorney, Agent, or Firm*—Townsend and Townsend and Crew LLP

(57) ABSTRACT

Surgical sponges and other articles are provided with machine-readable information which provides a serial number or other unique identification of the sponge. In addition, the machine-readable information will provide the type of article and/or a characteristic visual motif associated with the article. That way, by scanning in the machine-readable information from the sponges or other articles prior to a procedure, the computer or other digital processor can determine which articles may be missing after the procedure and alert the surgical team as to the type and/or characteristic visual motif of the missing article.

5 Claims, 5 Drawing Sheets

U.S. PATENT DOCUMENTS

| | | | |
|---|---|---|---|
| 3,965,907 A | 6/1976 | Hardy et al. | |
| 4,098,728 A | 7/1978 | Rosenblatt | |
| 4,114,601 A | 9/1978 | Abels | |
| 4,244,369 A | 1/1981 | McAvinn et al. | |
| 4,264,575 A | 4/1981 | Zimmerman et al. | |
| 4,477,256 A | 10/1984 | Hirsch | |
| 4,626,251 A | 12/1986 | Shen | |
| 4,639,253 A | 1/1987 | Dyer et al. | |
| 4,645,499 A | 2/1987 | Rupinskas | |
| 4,658,818 A | 4/1987 | Miller, Jr. et al. | |
| 4,711,996 A | 12/1987 | Drexler | |
| 4,718,897 A | 1/1988 | Elves | |
| 4,832,198 A | 5/1989 | Alikhan | |
| 4,917,694 A | 4/1990 | Jessup | |
| 5,031,642 A | 7/1991 | Nosek | |
| 5,041,103 A | 8/1991 | Rupinskas | |
| 5,045,080 A | 9/1991 | Dyer et al. | |
| 5,049,219 A | 9/1991 | Johns et al. | |
| 5,057,095 A | 10/1991 | Fabian | |
| 5,074,840 A | 12/1991 | Yoon | |
| 5,112,325 A | 5/1992 | Zachry | |
| 5,231,273 A | 7/1993 | Caswell et al. | |
| 5,374,813 A | 12/1994 | Shipp | |
| 5,443,082 A | 8/1995 | Mewburn | |
| 5,456,718 A | 10/1995 | Szymaitis | |
| 5,610,811 A | 3/1997 | Honda | |
| 5,629,498 A | 5/1997 | Pollock et al. | |
| 5,637,850 A | 6/1997 | Honda | |
| 5,650,596 A | 7/1997 | Morris et al. | |
| 5,678,569 A | 10/1997 | Chew et al. | |
| 5,805,451 A | 9/1998 | Speas et al. | |
| 5,923,001 A | 7/1999 | Morris et al. | |
| 5,931,824 A * | 8/1999 | Stewart et al. | 604/358 |
| 5,991,728 A | 11/1999 | DeBusk et al. | |
| 6,671,698 B2 * | 12/2003 | Pickett et al. | 1/1 |
| 7,116,227 B2 * | 10/2006 | Eckstein et al. | 340/571 |
| 7,124,941 B1 * | 10/2006 | O'Connell | 235/385 |
| 7,142,110 B2 * | 11/2006 | Schmidtberg et al. | 340/539.27 |
| 2002/0049650 A1 | 4/2002 | Reff | |
| 2002/0091593 A1 * | 7/2002 | Fowler | 705/28 |
| 2006/0249588 A1 * | 11/2006 | Walmsley et al. | 235/494 |

FOREIGN PATENT DOCUMENTS

| | | |
|---|---|---|
| WO | WO 94/22580 | 10/1994 |
| WO | WO 98/30166 | 7/1998 |

OTHER PUBLICATIONS

International Search Report and Written Opinion of PCT Application No. PCT/US06/40011, dated May 28, 2008, 10 pages.

* cited by examiner

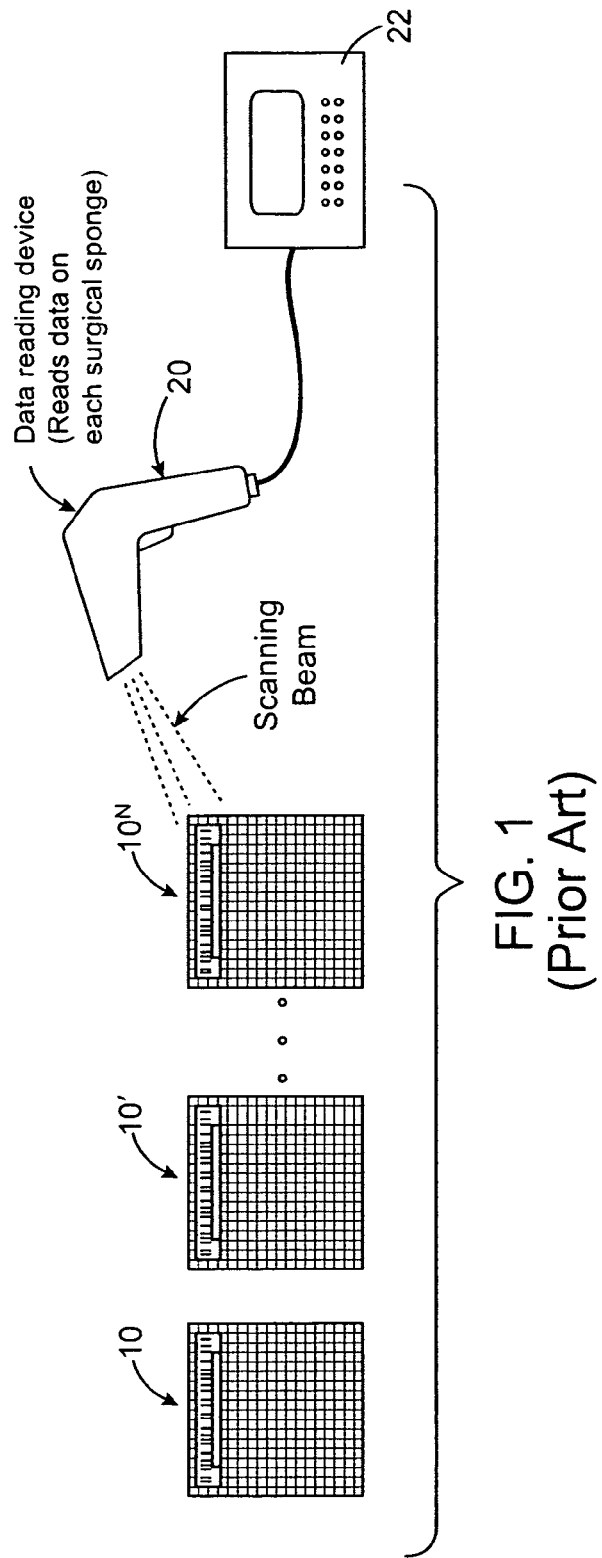
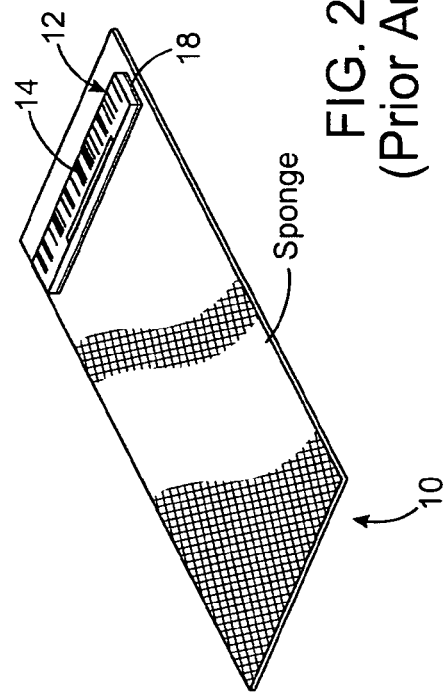
FIG. 1 (Prior Art)
FIG. 2 (Prior Art)

SYSTEMS AND METHODS FOR COUNTING SURGICAL IMPLEMENTS

This application claims the benefit of prior Provisional Application 60/725,960 filed on Oct. 11, 2005, the full disclosure of which is incorporated herein by reference.

BACKGROUND OF THE INVENTION

1. Field of the Invention.

The present invention relates generally to medical methods and apparatus. More particularly, the present invention relates to methods for locating and identifying surgical articles which have not been accounted for at the end of the surgical procedure.

Surgical sponges and other gauze articles are used to absorb blood and other body fluids during surgery. Many individual sponges can be used in a single procedure, and all the sponges which are used must be removed from the patient prior to closing an incision at the end of the procedure.

When used in a surgical procedure, sponges and other gauze articles become saturated with blood, alter in size and shape, and become difficult to visually distinguish from body tissue and from each other. Thus, while it might seem an easy task to locate and remove all sponges and other gauze articles from a patient at the end of surgery, the sponges are very hard to identify and difficult to count when they adhere to each other when soaked with blood. The task of accounting for sponges is even more difficult and more complex in surgical procedures where large numbers of sponges of many sizes and types may be used. Errors can occur when sponges are miscounted during initial counts and/or subsequent counts. When a subsequent count does not match a previous count, a recount is typically taken. Potentially more serious, a single sponge can mistakenly be counted more than once, raising the possibility a count can be incorrectly considered accurate allowing the patient to be closed with a sponge still at the operative site.

An improved method and system for accounting and identifying surgical sponges is described in U.S. Pat. No. 5,931,824, which is commonly assigned with the present application and which is incorporated herein by reference. As shown in FIGS. 1 and 2, which are taken from this patent, each sponge 10 used in a procedure is provided with a substrate or label 12 which includes machine-readable information 14, typically in the form of a bar code. If a total of N sponges are to be set aside for use in a procedure, each of the sponges 10, 10', ... $10^N$ will have a label 12 with unique label identification provided by the machine-readable information 14. Thus, the sponges 10 or other surgical articles may be scanned using a hand-held or other scanner 20, and the identification information stored in a computer 22 or other digital microprocessor-based unit. By scanning the identification of all sponges or other articles 10 to be used prior to the procedure and then scanning all sponges 10 as they are being removed from the patient after the procedure (as well as any sponges which might not have been used), the computer 22 can compare a compilation of the original group of sponges with the group of removed and unused sponges to determine if any sponges are missing and unaccounted for. If a sponge is accidentally scanned more than once, the computer will recognize the error and only allow each individual sponge to be counted in once and out once.

If the system of the '824 patent determines that all sponges have been accounted for after sponge removal, then it will be certain that all sponges have indeed been removed and the patient is ready to be surgically closed. If, however, the system indicates that one or more sponges are missing, it is necessary for the nurses and surgeons to visually inspect the surgical site in an attempt to locate the missing sponge(s). If they cannot locate the sponge(s) in the surgical site, then they must recount and rescan the removed sponges which are bloodied and difficult to separate. It will be necessary to separate and rescan each individual sponge until the system scans the missing sponge(s), indicating that the count is complete. Such recounts can take significant time and effort, but must be undertaken perhaps multiple times until the count is complete.

For these reasons, it would be desirable to provide improved methods and systems for scanning machine-readable information on surgical sponges and other articles which are used in surgical procedures. It would be particularly advantageous if the methods and systems could provide information relating to the particular missing article(s) which would assist the surgical team in performing recounts and visually identifying the missing article(s). At least some of these objectives will be met by the inventions described and claimed hereinbelow.

2. Description of the Background Art.

U.S. Pat. No. 5,931,824 has been discussed above. Other pertinent patents and published applications include U.S. Pat. Nos. 3,941,132; 3,965,907; 4,098,728; 4,114,601; 4,244,369; 4,264,575; 4,477,256; 4,626,251; 4,639,253; 4,645,499; 4,658,818; 4,711;996; 4,718,897; 4,832,198; 4,917,694; 5,031,642; 5,041,103; 5,045,080; 5,049,219; 5,057,095; 5,074,840; 5,112,325; 5,231,273; 5,374,813; 5,443,082; 5,456,718; 5,610,811; 5,629,498; 5,650,596; 5,637,850; 5,678,569; 5,805,451; 5,923,001; 5,991,728; U.S. Publ. 2002/0049650; WO 94/22580; WO 98/30166; and EP 0948940.

BRIEF SUMMARY OF THE INVENTION

The present invention provides improved methods and systems for assisting in locating surgical articles unaccounted for after a surgical procedure. The present invention relies on alerting the surgical team of certain readily discernable visual characteristics of the missing articles in order to facilitate locating those articles in the patient or in the collection of used articles. By knowing the visual characteristic of the missing sponge or other surgical article, the task of visually searching for the missing article(s) is greatly simplified.

More particularly, the methods and systems of the present invention will alert the surgical team and display or otherwise provide information concerning the type of the missing article, a visual motif characteristic of the missing article, or the like. In the case of surgical sponges and other gauze particles, the type will usually comprise the size, shape, or other inherent visually discernable property of that article. The "visual motif" in contrast, will typically be a color, pattern, or other visually discernable characteristic which is specifically introduced or imparted to the article for the primary or sole purpose of making that article readily distinguishable from otherwise similar articles. Such visual motifs may be applied to the entire article, for example by dying, painting, inscribing, patterning, or otherwise imparting the desired color or pattern to that article. Alternatively, the visual motif may be applied using a separate label, layer, woven element, border, or the like.

The sponges, gauze articles, or other articles of the present invention will usually further include machine-readable information of a type as generally described in U.S. Pat. No. 5,931,824, previously incorporated herein by reference. The machine-readable information will include a unique serial number or other information which will distinguish that article from each and every other article which may be included in a system of articles intended for use in a single surgical procedure. Machine-readable information will usually be optically encoded, such as a bar code or a two-dimensional code, such as a Datamatrix® pattern, but could also be electronically, sonically, or otherwise interrogable and readable. For example, the identifying information could be in the form of a radio frequency identification tag (RFID).

In addition to the serial number and/or other unique article identification, the machine-readable information on the articles of the present invention will also include information regarding the appearance of the article to assist in visually searching for the article should it become missing during a surgical procedure. Most simply, the machine-readable information could indicate the type of article to which the information is attached. Alternatively or additionally, the machine-readable information could include the identity of a characteristic visual motif of the article to which the information is attached. In this way, by scanning in the machine-readable information prior to a surgical procedure, the computer or other control system will be able to store not only the serial number or other identifying information for each article, but also will associate that identification information with the type and/or visual motif of the particular article. Thus, when the system later fails to account for a particular article after a surgical procedure, the system can display or otherwise alert the surgical team of the type and/or visual motif of the "unaccounted" article in order to facilitate visually locating that article in the patient or in the collection of removed articles.

In a first specific aspect of the present invention, a method for locating surgical articles unaccounted after a surgical procedure comprises determining if one or more surgical articles are missing after the procedure. If an article is missing, a characteristic type and/or visual motif for each of the missing surgical articles is provided to the surgical team. The surgical team is then able to visually search the patient and the removed articles in order to locate the unaccounted surgical articles based on the type and/or characteristic visual motif.

The steps of determining and providing in this method are usually performed by a computer or other digital processor. The computer tracks all articles used in the procedure and compares the identity of each article to be used in the procedure with the identity of each article removed after the procedure (or unused in the procedure). By tracking the type and/or characteristic visual motif of each individual article, the computer can display the type and/or characteristic visual motif to the surgical team in order to facilitate visually searching for the missing article.

Useful, common visual motifs include color of at least a portion of the article, a pattern formed over at least a portion of the article, a color provided on at least a portion of a label which is affixed to the article, and/or a pattern formed on at least a portion of a label affixed to the article. The characteristic visual motif will be different on at least some of the articles so that the articles may be visually distinguished from each other. While in some cases it may be desirable that the characteristic visual motif is different on each and every article employed in a surgical procedure, it will not always be practical to provide such a large number of distinguishable visual motifs. Practically, however, there will usually be at least three distinguishable visual motifs which are available to apply to different articles, usually being at least five distinguishable vessels motifs, and often at least eight distinguishable visual motifs available for applying to different articles, and optionally much greater numbers might be used.

In this way, the task of recounting and rescanning articles can be greatly simplified since only those articles of the identified type and/or visual motif need be separated and scanned.

In a second aspect of the present invention, a method for accounting for surgical articles used in a surgical procedure comprises providing a plurality of articles for the procedure where each article has a type and/or a characteristic visual motif. Each article further carries machine-readable information where the information includes identification of the article including the type and/or the visual motif. Prior to the procedure, the machine-readable information on each article is scanned into a list or compilation of articles used maintained on the computer. After the procedure is complete and the used article is removed, the machine-readable information on each of the articles used in the procedure and removed from the patient is scanned to produce a list or compilation of articles removed. Scanned information is compiled in the computer which compares the list of articles removed with the list of articles scanned in prior to the procedure to identify any individual articles which have not been accounted for. The computer displays the type and/or characteristic visual motif for at least some of the unaccounted articles, typically all of the unaccounted articles, to help visually distinguish the unaccounted articles from other articles to facilitate searching for the unaccounted articles in the group of articles removed.

Usually, the machine-readable information will include at the least a visual motif which will comprise color of at least a portion of the articles, a pattern on at least a portion of the article, a color at least a portion of a label, and/or a pattern on at least a portion of the label. There may be a fixed number of different characteristic visual motifs which are distributed among all of the articles used in the procedure.

In such cases, there will usually be no correlation between type of article and the characteristic visual motif possessed by the article. Alternatively, the characteristic visual motif may be applied to articles of each type so that the visual motif will be the same for all articles of each type. For example, all sponges or other gauze articles of one size may have the same visual motif applied thereto.

In addition to the methods described above, the present invention further provides systems of surgical articles. The systems typically comprise a plurality of sponges or other gauze articles and may include all articles intended for use in a particular surgical procedure, optionally including articles of different sizes or other types. Each article of the plurality of individual surgical articles will include machine-readable information thereon. The machine-readable information on each article will provide information which uniquely identifies that particular article from among all of the other articles in the system. The machine-readable information will further include information which identifies the type of the particular article and/or a characteristic visual motif of that particular article. The machine-readable information may encode the article identification, article type, and characteristic visual motif information in a variety of ways. For example, the machine-readable information may include different fields where each field provides a different aspect of the information, i.e., one field includes the serial number, a second field includes the type information, and a third field includes the identification of the characteristic visual motif. Alternatively, the machine-readable information may simply comprise serial numbers, where the computer or other digital processor can access or look up a table which provides all of the identification, type, and visual motif information related to the particular article having that serial number. Other methods for encoding the desired information will also be possible.

The systems may optionally be provided in packages of multiple articles. For example, surgical sponges or other gauze articles may be packaged together in groups of five, ten, twenty or more. In such cases, the packages themselves may provide machine-readable information which identifies to the digital processor all the information located on each of the individual articles within the package. Thus, by scanning the package containing a plurality of surgical articles prior to a surgical procedure, the computer or other digital processor may acquire all information concerning the identification, type, and visual motif of each individual article within the package. This is advantageous source it can reduce or eliminate the need to scan each individual sponge on other article before the procedure.

BRIEF DESCRIPTION OF THE DRAWINGS

FIGS. 1 and 2 illustrate prior art systems as discussed in the Background of the Invention.

DETAILED DESCRIPTION OF THE INVENTION

The present invention can be used to track and account for any type of surgical article used in a surgical procedure. Most often, however, the articles will comprise surgical sponges, which are gauze articles which come in different sizes and shapes. According to the present invention, each gauze or other article will be labeled with machine-readable information which can provide two, three or more distinct pieces of information regarding the labeled articles. The machine-readable information will always include a serial number or other "unique identification" which distinguishes that article from all other articles which are or could be used in that procedure. Additionally, the machine-readable information will usually further include information as to the type of article, such as sponge size, and may further include identification of a characteristic "visual motif" possessed by the article. The machine-readable information is usually provided by an optically readable label which is affixed directly to a surface of the sponge or other surgical article. Alternatively, the information could be provided by radiofrequency identification tags or other electronic or acoustic data storage devices incorporated in or on the article. The articles will optionally further include human readable information corresponding to all or at least a part of the machine-readable information on the article.

In the case of optically readable labels, a scanning system such as that illustrated in FIG. 1 can be used to acquire the information and input the information into a computer or other digital processor. The scanning system will be used both before a procedure in order to scan in information on the articles being used (optionally employing package labels as described hereinafter with reference to FIG. 7) and will further be used after the procedure in order to scan both removed and unused articles to assure that all individual articles have been removed from the patient.

Figure 3:
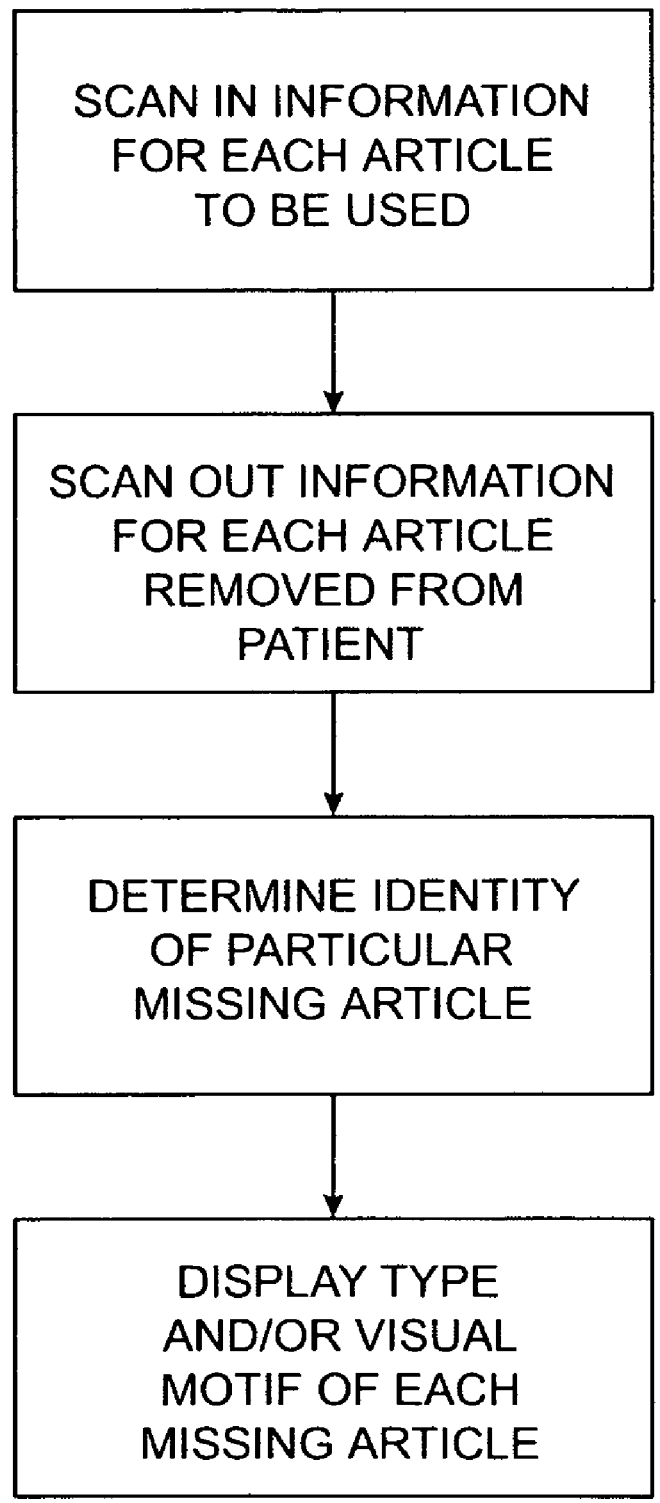
FIG. 3 is a block diagram illustrating the method steps of the present invention.

Thus, referring to FIG. 3, a first step in the methods of the present invention will be to scan in information on the articles to be used. After the information is scanned in and stored in the computer or other digital processor, the surgery is performed using the individual articles, and during and after the procedure is complete the articles will be removed from the patient and collected for disposal. As the articles are removed, the individual removed articles are scanned out of the system so that the system keeps track of the removed articles. The system can compare the articles which have been scanned in for use with those which have been removed from the patient and which were unused to determine if there are any individual articles not accounted for. Alternatively, the system could maintain a running count, decrementing each article as it is removed and displaying the remaining count so that the physician will know immediately when the last sponge has been removed. If articles are not accounted for, the system can then display type and/or visual motif information for each unaccounted article. For example, the system can indicate that a certain number of articles of particular sizes have not been accounted for. Alternatively or additionally, the system can identify the characteristic visual motif of the unaccounted articles.

After the type and/or visual motif of the unaccounted articles has been displayed, the surgical team can search the surgical site and the collection of used and unused surgical sponges in order to locate those of the displayed type or having the displayed visual motif. The surgical team then need rescan only those articles of the identified type and/or visual motif, thus greatly reducing the amount of rescanning necessary to locate the unaccounted articles.

Figure 4:
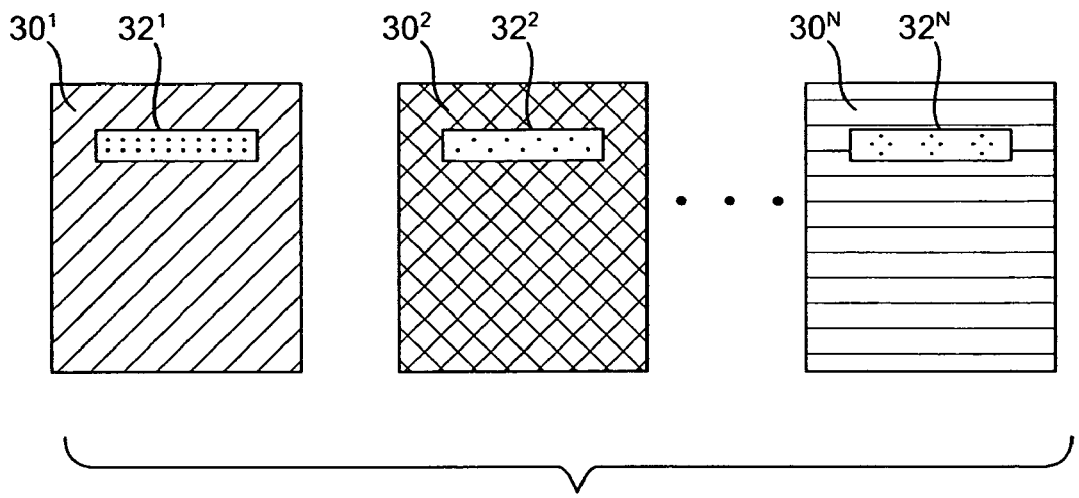
FIGS. 4 through 6 illustrate surgical article systems with each article marked in accordance with the present invention.

Sponge systems according to the present invention will comprise a plurality of individual sponges or other gauze articles, such as sponges 30 shown in FIG. 4. As shown in FIG. 4, the sponges are all of one size or type and each include unique machine-readable information on labels $32^1$-$32^N$. Each of the sponges 30, 30$^1$, and 30$^N$ have different colors or patterns as indicated by the different cross-hatching in FIG. 4. By providing at least three different colors or patterns, often at least five different colors or patterns, preferably at least eight different colors or patterns, the task of looking for any particular sponge 30 from among a group of used, soiled sponges will be greatly facilitated.

Figure 5:
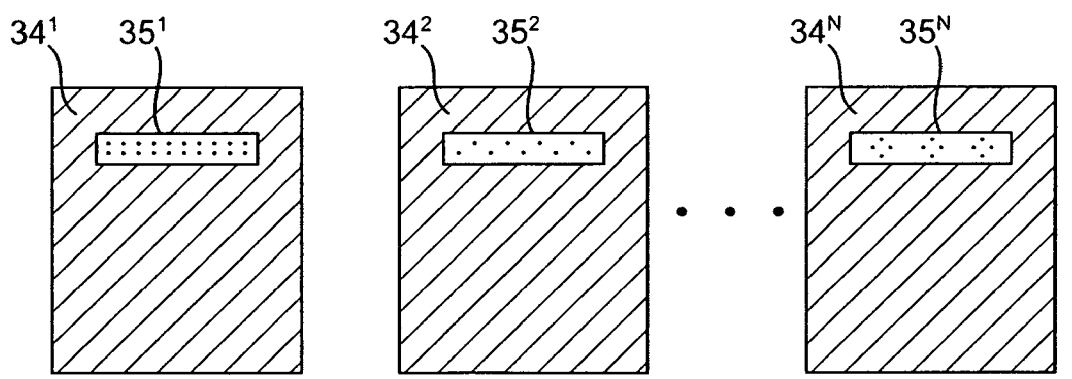
Figure 5:
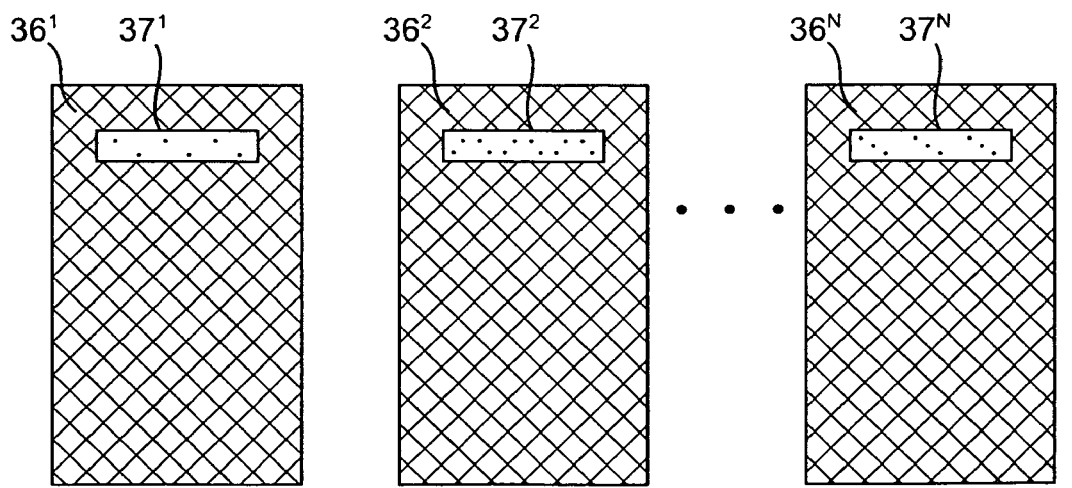

Referring now to FIG. 5, the systems of the present invention may include sponges or other gauze articles having different sizes or other types. For example, gauze articles $34^1$-$34^N$ may have a first size, such as 4 in.×4 in., while a second plurality of sponges $36^1$-$36^N$ may have a different size, for example 4 in.×8 in. Each of the sponges 34 and 36 will have a label $35^1$-$35^N$ and $37^1$-$37^N$, respectively, which includes unique identification information distinguishing the labeled sponge from each and every other sponge in the system, regardless of size. The information on labels $35^1$, $35^2$ through $35^N$, however, will all include information indicating the size or other type information, and that information will be the same on each of those labels. Similarly, each of the labels $37^1$, $37^2$ through $37^N$ on articles 36 will also include size or type information which is the same for all of those articles. While the motifs for the sponges in the system of FIG. 5 could all have been different, as illustrated the motifs for sponges 34 are all the same while the motifs for sponges $36^1$-$36^N$ are all the same but different from that of sponges $34^1$-$34^N$.

Figure 6:
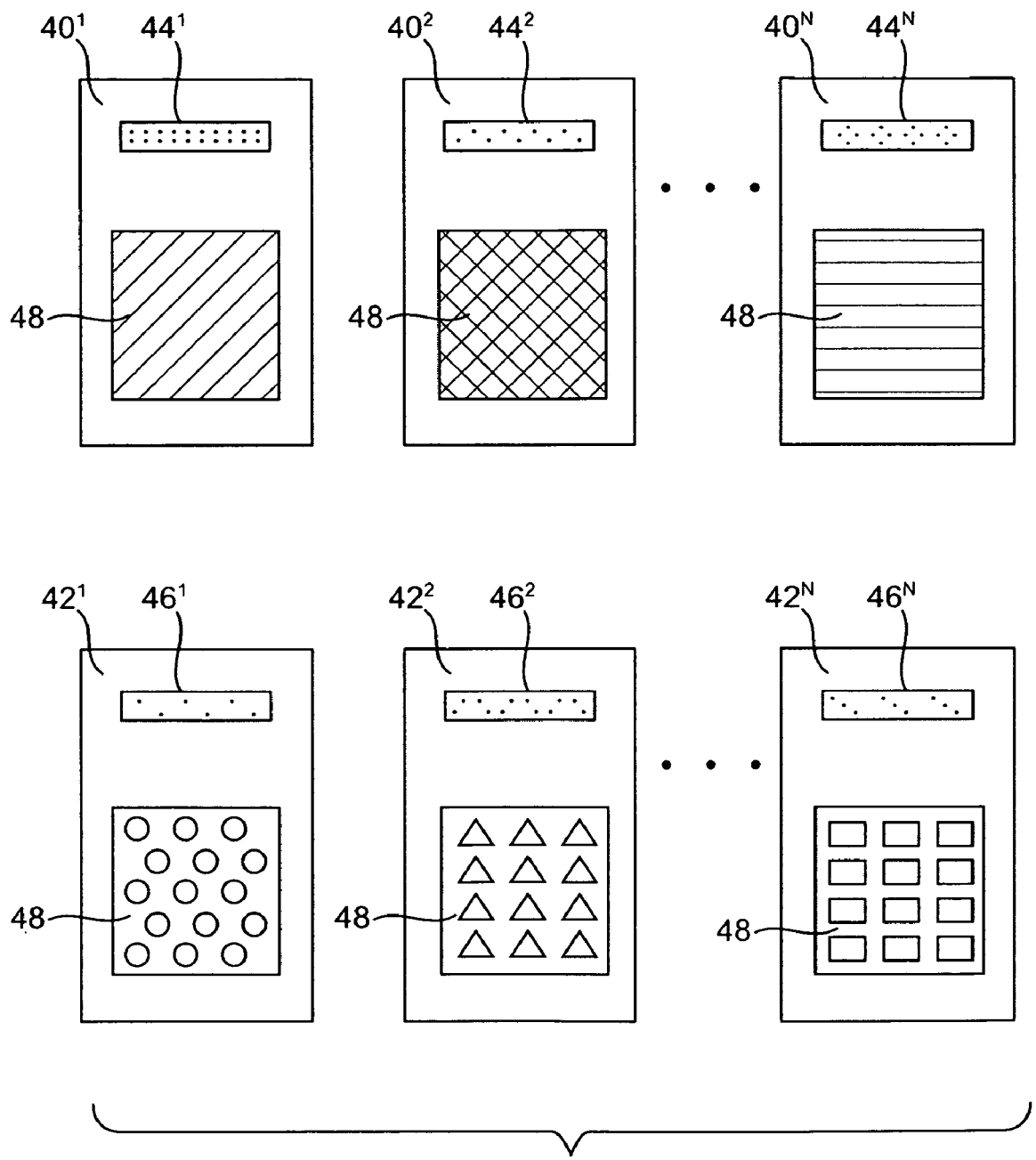

Referring now to FIG. 6, a further sponge system includes sponges $40^1$-$40^N$ of a first size or type and sponges $42^1$-$42^N$ of a second size or type. The sponges further include label information $44^1$-$44^N$ and $46^1$-$46^N$, respectively, identifying the sponge uniquely with respect to all other sponges in the system as well as identifying the size or other sponge type of the particular sponge. In the system of FIG. 6, the sponges further include labels 48, each of which has a unique color, pattern, or other visually discernable characteristic which permits each sponge in the system to be visually distinguished from each and every other sponge in the system. The nature of the visual motif on each label 48 will be included in the information on labels $44^1$-$44^N$ and $46^1$-$46^N$ so that, when the computer or other digital processor determines that a particular sponge is missing, it can display the visual motif on the label of the missing sponge.

Note that while the labels 48 on the system of FIG. 6 are shown to be separate from the identification labels 44 and 46, it would certainly be possible to provide both the machine-readable information and the visual motif on a single label which is affixed to the sponge or other surgical article.

Figure 7:
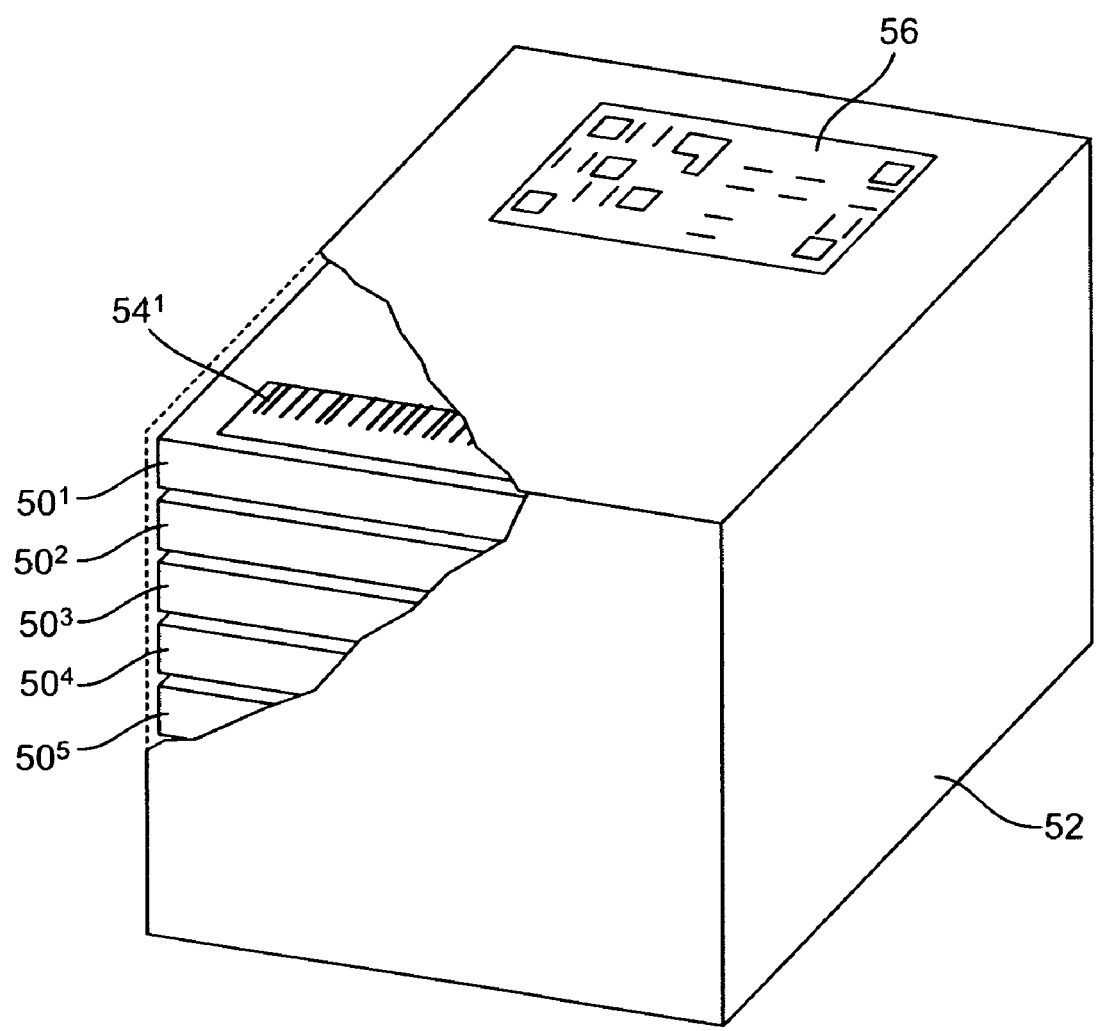
FIG. 7 illustrates a surgical article system with a common package identification code on a single label.

Referring now to FIG. 7, individual sponges or other articles 50 may be packaged in a common package 52, such as a plastic or other wrap. Each of the individual sponges or other articles 50 will have an individual label 54 including all of the identification numbers (e.g. serial number), type, and visual motif information discussed above. In addition, the package 52 may possess an additional label 56 having machine-readable information which includes most or all of the information from each and every label 54 on the individual sponges or other articles 50. In this way, the package label 56 can be scanned once in order to provide at least the identification, type, and visual motif information from the individual sponges or other articles 50 to the computer or other distal scanning system of the present invention. The individual labels 54 will be needed, of course, for scanning the individual sponges or other articles 50 as they are removed from the patient or if they have been unused in the procedure.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for accounting for gauze surgical articles used in a surgical procedure, said method comprising:

providing a plurality of the gauze articles each displaying machine-readable information and having a characteristic visual motif in addition to the machine-readable information, wherein the characteristic visual motif of some but not all of the articles will differ from the characteristic visual motif of others of the articles and wherein said machine-readable information on each article includes both (1) data uniquely identifying that article so that it may be distinguished from all other articles used in the procedure, and (2) data identifying the visual motif of the article wherein the characteristic visual motif comprises at least one of color of at least a portion of the article, a pattern on at least a portion of the article, a color on at least a portion of a label, and a pattern on at least a portion of the label;

before the procedure begins, scanning into a computer the machine-readable information of each of the gauze surgical articles available to be used in the procedure to produce a list of gauze surgical articles available to be used;

introducing at least some of the gauze surgical articles available to be used to an operative site in a patient;

after the procedure ends, removing the gauze surgical articles from the operative site to produce a collection of removed gauze surgical articles;

scanning into the computer the machine-readable information of each of the gauze surgical articles removed from the patient and each of the gauze surgical articles not used in the procedure to produce a list of gauze surgical articles not used and removed;

wherein the computer:

compares (1) the list of gauze surgical articles not used and removed with (2) the list of gauze surgical articles available to be used to identify unaccounted gauze surgical articles; and displays the characteristic visual motif(s) for each of the unaccounted gauze surgical articles, wherein a user can visually distinguish each unaccounted gauze surgical article from other gauze surgical articles in the collection based on the characteristic visual motif;

said method further comprising rescanning only those removed gauze surgical articles having the displayed characteristic visual motif(s).

2. A method as in claim 1, wherein the gauze surgical articles include at least a first plurality of gauze surgical articles of a first size and a second plurality of gauze surgical articles of a second size, wherein each plurality has a characteristic visual motif which is common for that type, allowing the different types of gauze surgical to be visually distinguished.

3. A method as in claim 1, wherein a fixed number of different characteristic visual motifs are distributed among all of the gauze surgical articles used in the procedure, wherein said fixed number is at least three and is less than the total number of gauze surgical articles.

4. A method as in claim 3, wherein the fixed number is at least five.

5. A method as in claim 3, wherein the fixed number is at least eight.

* * * * *